US011357584B2

(12) United States Patent
Xu et al.

(10) Patent No.: US 11,357,584 B2
(45) Date of Patent: Jun. 14, 2022

(54) METHOD FOR DETECTING FAULTS IN OPERATING STATES OF SURGICAL ROBOTS

(71) Applicant: Beijing Surgerii Technology Co., Ltd., Beijing OT (CN)

(72) Inventors: Kai Xu, Beijing (CN); Bin Zhao, Beijing (CN); Zhengchen Dai, Beijing (CN); Jiangran Zhao, Beijing (CN); Huan Liu, Beijing (CN); Wukun Mei, Beijing (CN); Huichao Zhang, Beijing (CN); Wei Wei, Beijing (CN); Bo Liang, Beijing (CN)

(73) Assignee: BEIJING SURGERII TECHNOLOGY CO., LTD., Beijing (CN)

( * ) Notice: Subject to any disclaimer, the term of this patent is extended or adjusted under 35 U.S.C. 154(b) by 442 days.

(21) Appl. No.: 16/288,161

(22) Filed: Feb. 28, 2019

(65) Prior Publication Data

US 2019/0192246 A1    Jun. 27, 2019

Related U.S. Application Data

(63) Continuation of application No. PCT/CN2017/099848, filed on Aug. 31, 2017.

(30) Foreign Application Priority Data

| Aug. 31, 2016 | (CN) | 201610798120.X |
| Aug. 31, 2016 | (CN) | 201610798121.4 |
| Aug. 31, 2016 | (CN) | 201610799313.7 |

(51) Int. Cl.
| *A61B 34/35* | (2016.01) |
| *A61B 34/37* | (2016.01) |
| *G01R 31/00* | (2006.01) |
| *A61B 34/20* | (2016.01) |
| *B25J 3/00* | (2006.01) |
| *B25J 19/00* | (2006.01) |
| *H04L 65/00* | (2022.01) |
| *H04W 84/20* | (2009.01) |
| *A61B 34/00* | (2016.01) |

(52) U.S. Cl.
CPC .............. *A61B 34/37* (2016.02); *A61B 34/20* (2016.02); *B25J 3/00* (2013.01); *B25J 19/00* (2013.01); *G01R 31/00* (2013.01); *H04L 65/00* (2013.01); *H04W 84/20* (2013.01); *A61B 34/70* (2016.02)

(58) Field of Classification Search
USPC ................................................ 700/245–264
See application file for complete search history.

(56) References Cited

U.S. PATENT DOCUMENTS

| 5,285,381 | A | * | 2/1994 | Iskarous | B25J 9/161 |
| | | | | | 714/E11.069 |
| 5,408,409 | A | * | 4/1995 | Glassman | A61F 2/46 |
| | | | | | 600/407 |
| 5,553,609 | A | * | 9/1996 | Chen | G16H 40/67 |
| | | | | | 348/E7.086 |
| 6,331,181 | B1 | * | 12/2001 | Tierney | A61B 34/37 |
| | | | | | 606/130 |
| 6,618,628 | B1 | * | 9/2003 | Davlin | G05B 19/0421 |
| | | | | | 700/20 |
| 7,730,362 | B2 | * | 6/2010 | Claus | G06F 13/385 |
| | | | | | 714/708 |
| 8,380,126 | B1 | * | 2/2013 | Ma | H04L 1/22 |
| | | | | | 455/509 |
| 8,868,238 | B1 | * | 10/2014 | Gray | G05D 1/0088 |
| | | | | | 901/1 |
| 9,622,826 | B2 | * | 4/2017 | Diolaiti | B25J 9/1633 |
| 10,820,949 | B2 | * | 11/2020 | Prisco | A61B 34/30 |
| 2002/0128552 | A1 | * | 9/2002 | Nowlin | A61B 34/35 |
| | | | | | 600/427 |
| 2004/0039485 | A1 | * | 2/2004 | Niemeyer | A61B 34/37 |
| | | | | | 700/245 |

(Continued)

FOREIGN PATENT DOCUMENTS

| CN | 1808885 A | 7/2006 |
| CN | 101870107 A | 10/2010 |

(Continued)

OTHER PUBLICATIONS

International Search Report of PCT/CN2017/099848.
The first Office Action of Chinese application 2016107981214.
The first Office Action of Chinese application 2016107993137.
Search report of Chinese application 201610798120X.
Search report of European application 178455002.
Office Action in corresponding Japanese Application No. 2019-531522, dated Nov. 2, 2021 (4 pages).

(Continued)

*Primary Examiner* — Jonathan L Sample
(74) *Attorney, Agent, or Firm* — Bayes PLLC

(57) ABSTRACT

This invention relates to a method for detecting faults in the operating states of a surgical robotic system, wherein the surgical robotic system including a master computer, a master embedded computer and a plurality of slave embedded computers is provided; the master computer controls the master embedded computer and the slave embedded computers via the LAN router; the master embedded computer communicates with the slave embedded computers via the LAN router and a first communication bus. In the present invention, the master computer, the master embedded computer and the slave embedded computers can detect faults interactively. Safety and reliability of the operation of the surgical robotic system can be improved without increasing any additional detection components, and communication burden of the system can be effectively reduced. The present invention can be widely applied to a minimally invasive surgical robotic system.

20 Claims, No Drawings

(56) References Cited

U.S. PATENT DOCUMENTS

| | | | | |
|---|---|---|---|---|
| 2004/0205420 | A1* | 10/2004 | Seeley | G06F 11/0772 714/57 |
| 2005/0188137 | A1* | 8/2005 | Fujiki | G06F 13/4217 710/110 |
| 2006/0145647 | A1* | 7/2006 | Kitatsuji | G05B 19/414 318/568.11 |
| 2006/0287769 | A1* | 12/2006 | Yanagita | B25J 9/1682 700/245 |
| 2007/0093939 | A1* | 4/2007 | Kobayashi | G05B 19/4185 700/245 |
| 2007/0249286 | A1* | 10/2007 | Ma | H04W 12/50 455/507 |
| 2010/0049268 | A1* | 2/2010 | Martins | G06F 11/2025 607/9 |
| 2010/0234857 | A1* | 9/2010 | Itkowitz | G09B 23/285 700/259 |
| 2010/0302214 | A1* | 12/2010 | Kim | H04N 13/398 345/204 |
| 2011/0295295 | A1* | 12/2011 | Shelton, IV | A61B 34/30 606/170 |
| 2011/0319714 | A1* | 12/2011 | Roelle | A61B 1/008 600/118 |
| 2012/0127145 | A1* | 5/2012 | Jang | G09G 3/20 345/204 |
| 2012/0316573 | A1* | 12/2012 | Durant | A61B 34/30 606/130 |
| 2013/0296737 | A1* | 11/2013 | Mcmillan | A61B 34/30 600/562 |
| 2014/0108896 | A1* | 4/2014 | Jung | G06F 11/08 714/819 |
| 2014/0257330 | A1* | 9/2014 | Choi | A61B 34/37 606/130 |
| 2015/0112481 | A1* | 4/2015 | Burns | B25J 9/1674 700/248 |
| 2015/0157411 | A1* | 6/2015 | Choi | A61B 34/37 606/130 |
| 2015/0224639 | A1* | 8/2015 | Dockter | B25J 3/04 700/264 |
| 2016/0193730 | A1* | 7/2016 | Kawase | B25J 9/1674 901/2 |

FOREIGN PATENT DOCUMENTS

| | | |
|---|---|---|
| CN | 102073284 A | 5/2011 |
| CN | 102280826 A | 12/2011 |
| CN | 102393656 A | 3/2012 |
| CN | 102802553 A | 11/2012 |
| CN | 103402714 A | 11/2013 |
| CN | 103596516 A | 2/2014 |
| CN | 103607968 A | 2/2014 |
| CN | 104260094 A | 1/2015 |
| CN | 104298235 A | 1/2015 |
| CN | 104582624 A | 4/2015 |
| CN | 104688347 A | 6/2015 |
| CN | 104828028 A | 8/2015 |
| CN | 106175936 A | 12/2016 |
| CN | 106272554 A | 1/2017 |
| CN | 106370949 A | 2/2017 |
| JP | H08286718 A | 11/1996 |
| JP | 2008544814 A | 12/2008 |
| JP | 2009525098 A | 7/2009 |
| JP | 2012071406 A | 4/2012 |
| JP | 2013034862 A | 2/2013 |
| WO | 2012166815 A1 | 12/2012 |
| WO | 2014005139 A2 | 1/2014 |
| WO | 2015148112 A1 | 10/2015 |
| WO | 2016077478 A1 | 5/2016 |
| WO | 2016098571 A1 | 6/2016 |

OTHER PUBLICATIONS

Search Report in corresponding Japanese Application No. 2019-531522 dated Apr. 12, 2021 (18 pages).
Canadian Office Action in corresponding Canadian Application No. 3,035,311 dated Sep. 8, 2021 (4 pages).

* cited by examiner

METHOD FOR DETECTING FAULTS IN OPERATING STATES OF SURGICAL ROBOTS

CROSS-REFERENCE TO RELATED APPLICATIONS

This patent application is a continuation of International Application No. 5 PCT/CN2017/099848, filed one Aug. 31, 2017, which claims the priorities of the following three Chinese patent applications filed on Aug. 31, 2016: Chinese patent application No. 201610798120.X, entitled "A METHOD FOR DETECTING FAULTS IN OPERATING STATES OF SURGICAL ROBOTS"; Chinese patent application No. 201610799313.7, entitled "A METHOD FOR DETECTING FAULTS IN INCOMPLETE OPERATING STATE OF SURGICAL ROBOTS"; and Chinese patent application No. 201610798121.4, entitled "A METHOD FOR DETECTING FAULTS IN FULL OPERATING STATE OF SURGICAL ROBOTS". The entire disclosures of the above applications are incorporated herein by reference.

TECHNICAL FIELD

The present invention relates to a method for detecting faults of surgical robots, in particular to a method for detecting faults in operating states of surgical robots.

BACKGROUND

In recent years, minimally invasive surgery (MIS) has become an important surgical method due to its small trauma area and rapid recovery. Surgical robotic systems have been widely applied in the field of minimally invasive surgery by the advantages of its clear stereoscopic vision feedback and dexterous manipulation. Among them, the Da Vinci surgical robots from Intuitive Surgical Inc. have achieved great success in the field of minimally invasive surgery. A surgical robotic system generally comprises a visual operating arm and a plurality of surgical operating arms. The surgeon inputs control commands by operating input devices and an interface. After processed by a plurality of control computer nodes that can communicate with each other, the control commands are sent to the visual operating arm and the surgical operating arms to enable actuations thereof to perform the minimally invasive surgery. The above multiple control computer nodes constitute a distributed computer system.

Since minimally invasive surgeries applied to the human body have strict requirements on safety of the surgical robotic systems, it is necessary to perform fault detection on the respective control computer nodes in real time, and take the safest countermeasures according to the faults. Existing surgical robotic systems employ additional detection signals to monitor in real time whether a control computer node has failed so that it will greatly increase communication burden of the system. At present, most systems adopt redundant equipments to take over faulty equipments at any time. This method causes waste of system resources. Further, the existing surgical robotic systems do not specifically propose a systematic solution regarding human body safety.

SUMMARY

In view of the above problems, an objective of the present invention is to provide a method for detecting faults in operating states of a surgical robot, which can improve safety and reliability of operations of a surgical robotic system without increasing additional detecting components.

In order to achieve the above objective, the present invention adopts the following technical solution: a method for detecting faults in operating states of a surgical robot, the operating states include a full operating state and an incomplete operating state, and the details are as follows:

1) fault detection of a master computer in a full operating state or an incomplete operating state: A1) the master computer has a fault in the full operating state: the master computer broadcasts a desired pose signal to a master embedded computer and a plurality of slave embedded computers, respectively, via a Local Area Network (LAN) router at a preset period, receives a null operation instruction signal transmitted from the master embedded computer at the preset period and simultaneously receives an actual pose signal transmitted from the respective slave embedded computers at the preset period; if the master embedded computer and the slave embedded computers do not receive the desired pose signal transmitted from the master computer via the LAN router within the preset period, and the master embedded computer does not receive a null operation response signal returned from the master computer via the LAN router, the master computer is considered to be faulty; B1) the master computer fails in an incomplete operating state: the master computer sends a null operation instruction signal to the master embedded computer and the plurality of slave embedded computers, respectively, via the LAN router at the preset period, and receives null operation response signals returned from the master embedded computer and the respective slave embedded computers at the preset period; if the master embedded computer and the slave embedded computers all do not receive the null operation instruction signal transmitted from the master computer via the LAN router within the preset period, the master computer is considered to be faulty;

2) fault detection of the master embedded computer in a full operating state or an incomplete operating state: A2) the master embedded computer has a fault in a full operating state: the master embedded computer receives a desired pose signal transmitted from the master computer at the preset period, and sends a null operation instruction signal to the master computer at the preset period and obtains a null operation response signal returned from the master computer; and simultaneously listens to a motor position control signal transmitted from the slave embedded computers via a first communication bus; if the master computer does not receive the null operation instruction signal transmitted from the master embedded computer via the LAN router within the preset period, the master embedded computer is considered to be faulty; B2) the master embedded computer fails in an incomplete operating state: the master embedded computer receives the null operation instruction signal transmitted from the master computer at the preset period and returns a null operation response signal to the master computer, and transmits, via the LAN router, the null operation instruction signal to the slave embedded computers at the preset period and receives null operation response signals returned from the respective embedded computers; if the master computer does not receive, via the LAN router, the null operation response signal returned from the master embedded computer within the preset period and the respective slave embedded computers do not receive the null operation instruction signal transmitted from the master embedded computer within the preset period, the master embedded computer is considered to be faulty;

3) fault detection of the slave embedded computers in a full operating state or an incomplete operating state: A3) the slave embedded computer has a fault in a full operating state: the respective slave embedded computers receive a desired pose signal transmitted from the master computer via the LAN router at the preset period and send actual pose signals to the master computer via the LAN router; and simultaneously send the motor position control signal to the surgical tool driving module or the imaging tool driving module via the first communication bus at the preset period; if the master computer does not receive the actual pose signal transmitted from a certain embedded computer via the LAN router within the preset period, and if the master embedded computer does not listen to the motor position control signal transmitted from the certain slave embedded computer via the first communication bus within the preset period, it is considered that the certain slave embedded computer fails; B3) the slave embedded computer has a fault in an incomplete operating state: the respective slave embedded computers receive null operation instruction signals transmitted from the master computer and the master embedded computer via the LAN router at the preset period, and return a null operation response signal to the master computer and the master embedded computer at the preset period; if the master computer does not receive the null operation response signal returned from a certain slave embedded computer via the LAN router within the preset period and if the master embedded computer does not receive the null operation response signal returned from the certain slave embedded computer within the preset period, the certain slave embedded computer is considered to be faulty.

Further, when the master computer fails, an alarm mechanism and an emergency stop mechanism are firstly employed for the surgical robotic system or merely the alarm mechanism is employed, and after executing a recovery mechanism on the master computer, the master computer continues to send a signal to the master embedded computer and the respective slave embedded computers via the LAN router. If the recovery mechanism executed on the master computer is unsuccessful, a manual operation mechanism is executed by the master embedded computer and the slave embedded computers are controlled via the LAN router so as to control actions of the surgical tool or the imaging tool.

Further, when the master embedded computer fails, the alarm mechanism and the emergency stop mechanism are firstly employed for the surgical robotic system or only the alarm mechanism is employed, and then the manual procedure is executed by the master computer so as to control actions of the surgical tool or the imaging tool via the use of the slave embedded computers.

Further, when the certain slave embedded computer fails, the alarm mechanism and the emergency stop mechanism are firstly employed for the surgical robotic system or only the alarm mechanism is employed, the manual procedure is executed by the master computer, the failed slave embedded computer is replaced with the main embedded computer, and the master computer controls actions of the surgical tool or the imaging tool via the use of the master embedded computer or the other slave embedded computers.

Further, the recovery mechanism means that: when the master computer fails, the master embedded computer waits for the master computer to restart and restore. After the master computer restores, the operator performs a status inquiry operation on an operation interface of the master computer, the master computer sends a status inquiry instruction to the master embedded computer via the LAN router, and after receiving the state response instruction transmitted from the main embedded computer, adjusts the state of the surgical robotic system to a state prior to the failure.

Further, the alarm mechanism specifically comprises: 1) when the master computer fails, the master embedded computer updates a corresponding master computer indicator light to an "error" display state via a second communication bus; (2) when the master embedded computer fails, the master computer automatically switches the operation interface to a manual operation interface and prompts the failure of the master embedded computer on the interface, and the master computer updates the corresponding master embedded computer indicator light to the "error" display state at the same time; (3) when a certain slave embedded computer fails, the master computer automatically switches the operation interface to the manual operation interface and prompts the failure of the certain slave embedded computer on the interface, and the master embedded computer updates a corresponding slave embedded computer indicator light to the "error" display state via the second communication bus.

Further, when the master computer, the master embedded computer or the slave embedded computer fails in a full operating state, for all of the scenarios the emergency stop mechanism needs to be enabled, wherein:

The emergency stop mechanism refers to: the slave embedded computer controls the surgical tool or the imaging tool, through the corresponding surgical tool driving module or the imaging tool driving module, to stop movement and maintain the current pose after receiving a "holding" command from the master computer or the main embedded computer; or, the emergency stop mechanism refers to: the main embedded computer, instead of the failed slave embedded computer, controls the surgical tool or the imaging tool, through the corresponding surgical tool driving module or imaging tool driving module, to stop movement and maintain the current pose after receiving the "holding" command from the master computer.

Further, the manual procedure refers to: directly controlling the master computer, the master embedded computer or the slave embedded computers through a joint-parameter manual adjustment region of the surgical robot, and further controlling actions of the surgical tool or the imaging tool through the corresponding surgical tool driving module or imaging tool driving module.

In detail, the process is as follows:

when the master computer fails, the master embedded computer switches to a manual operation interface, directly controls the respective slave embedded computers through the joint-parameter manual adjustment region, and in turn controls actions of the surgical tool or the imaging tool through the surgical tool driving module or the imaging tool driving module;

when the master embedded computer fails, the master computer switches to the manual operation interface, directly controls the respective slave embedded computers through the joint-parameter manual adjustment region, and in turn controls the actions of the surgical tool or the imaging tool through the surgical tool driving module or the imaging tool driving module;

when the certain slave embedded computer fails, the master computer switches to the manual operation interface, the master embedded computer takes over the failed slave embedded computer, and the master computer directly controls the master embedded computer and the remaining non-faulty slave embedded computers through the joint-parameter manual adjustment region, and in turn controls actions of the surgical tool or the imaging tool through the surgical tool driving module or the imaging tool driving module.

Further, an upper level computer controls the surgical tool driving module and in turn controls actions of the surgical tool through the master embedded computer used to take over the failed slave embedded computer or through the functional salve embedded computer, wherein the upper level computer is the master computer or the master embedded computer.

When the surgical robot is in a full operating state or an incomplete operating state, in case that i) the master computer fails, ii) the slave embedded computer that controls actions of the surgical tool is functional, and iii) the master embedded computer is used as the master computer, control of the actions of the surgical tool is described as follows: the operator operates the pose of the surgical tool driving module to be controlled in a control-mapping selection area of the joint-parameter manual adjustment region, the master embedded computer reads out the joint parameters of the surgical arm at a preset period, and sends the generated desired pose to the slave embedded computer;

when the surgical robot is in a full operating state, the slave embedded computer receives the desired pose signal and performs closed-loop control over a pose of the surgical end effector at an end of the surgical tool through the surgical tool driving module.

In detail, the sequence is as follows:

a1) if the surgical arm carrying the surgical end effector at the end of the surgical tool is in an unfolded state, the surgical tool driving module drives the surgical end effector at the end of the surgical tool to maintain the current position and pose, restores its initial state, and drives the surgical arm back straight. Then the process proceeds to step a2);

a2) if the surgical end effector carried at the end of the surgical tool is not in its initial position and the surgical arm is in a straight state, the surgical tool driving module drives the surgical end effector at the end of the surgical tool to be directly withdrawn from a surgical incision in a patient back to its initial position. And then the process proceeds to step a3);

a3) the operator offloads the surgical tool from the surgical tool driving module to achieve separation of the surgical tool from the surgical robot.

When the surgical robot is in an incomplete operating state, the slave embedded computer receives the desired pose signal and controls the pose of the surgical end effector at the end of the surgical tool through the surgical tool driving module. The sequence in detail is as follows:

a1) if the surgical arm carrying the surgical end effector at the end of the surgical tool is in an unfolded state, the surgical tool driving module drives the surgical arm back straight. Then the process proceeds to step a2);

a2) if the surgical end effector carried at the end of the surgical tool is not in its initial position and the surgical arm is in a straight state, the surgical tool driving module drives the surgical end effector at the end of the surgical tool to be directly withdrawn from the surgical incision in a patient back to its initial position. Then the process proceeds to step a3);

a3) the operator offloads the surgical tool from the surgical tool driving module to achieve separation of the surgical tool from the surgical robot.

Further, when the surgical tool is withdrawn from the surgical incision in the patient to achieve entire separation of the surgical tool from the surgical robot, the upper level computer controls the imaging tool driving module and in turn controls actions of the imaging tool by controlling the master embedded computer used to take over the failed slave embedded computer or the functional slave embedded computer;

when the surgical robot is in a full operating state or an incomplete operating state, in case that i) a certain slave embedded computer controlling actions of the imaging tool fails, and ii) the master embedded computer is used to take over the failed slave embedded computer, control of the actions of the imaging tool is described as follows: the operator operates the imaging tool driving module to be controlled in the mapping selection area of the joint-parameter manual adjustment region, the master computer reads out the joint parameters of the surgical arm at the preset period and sends the generated desired pose to the master embedded computer.

When the surgical robot is in a full operating state, the master embedded computer receives the desired pose signal and performs closed-loop control of the pose of the imaging illumination module at the end of the imaging tool through the imaging tool driving module. In detail, the sequence is as follows:

b1) if the surgical arm carrying the imaging illumination module at the end of the imaging tool is in an unfolded state, the imaging tool driving module drives the imaging illumination module at the end of the imaging tool to maintain the current position and pose, and drives the surgical arm to straight back. Then the process proceeds to step b2);

b2) if the imaging illumination module carried at the end of the imaging tool is not in its initial position and the surgical arm is in a straight state, the imaging tool driving module drives the imaging illumination module at the end of the imaging tool to be directly withdrawn from the surgical incision in the patient to its initial position. Then the process proceeds to step b3);

b3) the operator offloads the imaging tool from the imaging tool driving module to achieve separation of the imaging tool from the surgical robot.

When the surgical robot is in an incomplete operating state, the master embedded computer receives the desired pose signal and controls the pose of the imaging illumination module at the end of the imaging tool through the imaging tool driving module. The sequence in detail is as follows:

b1) if the surgical arm carrying the imaging illumination module at the end of the imaging tool is in an unfolded state, the imaging tool driving module drives the surgical arm to straight back. Then the process proceeds to step b2);

b2) if the imaging illumination module carried at the end of the imaging tool is not in its initial position and the surgical arm is in a straight state, the imaging tool driving module drives the imaging illumination module at the end of the imaging tool to be directly withdrawn from the surgical incision in the patient to its initial position. Then the process proceeds to step b3);

b3) the operator offloads the imaging tool from the imaging tool driving module to achieve separation of the imaging tool from the surgical robot.

The present invention has the following advantages by employing the above technical solutions:

1. when the surgical robotic system is in a full operating state or an incomplete operating state, the invention can improve safety and reliability of the operation of the surgical robotic system without adding any additional detection components and effectively reduce communication burden of the system, by using a method for mutually detecting faults among the master computer, the master embedded computer and the salve embedded computers in the surgical robotic system.

2. The master embedded computer of the present invention is used to record the operating states of the surgical robotic system, and at the same time the master embedded computer can be used as a redundant slave embedded computer, so that when the certain slave embedded computer fails, the master embedded computer can replace the failed slave embedded computer.

3. When the master computer, the master embedded computer or the slave embedded computer in the surgical robotic system fails, the present invention can achieve fault recovery by employing a preset security mechanism to assist in withdrawing a part of the surgical robot inserted in the patient's body, which can further improve safety of the surgical robotic system.

This present invention can be widely applied to a minimally invasive surgical robotic system.

DETAILED DESCRIPTION

The invention is described in detail below by means of specific embodiments. However, it should be understood that the embodiments are provided for a better understanding of the present invention and are not to be construed as limiting the invention. The meaning of "/" in the embodiments is "or".

A surgical robotic system comprises a master computer, a master embedded computer and a plurality of slave embedded computers; the master computer controls the master embedded computer and the slave embedded computers via a LAN router, and the master embedded computer can communicate with the slave embedded computers via the LAN router and a first communication bus, wherein the first communication bus is preferably a CAN bus.

The operating states of the surgical robot of the present invention comprise a full operating state and an incomplete operating state, wherein the full operating state is defined as: the master computer continuously transmits a desired pose signal to the master embedded computer and the respective slave embedded computers via the LAN router, any of the slave embedded computers sends a motor position control signal to the surgical tool driving module/imaging tool driving module via the first communication bus so as to control actions of the surgical tool/imaging tool, and any of the slave embedded computers continuously sends an actual pose signal to the master computer via the LAN router.

The incomplete operating state is defined as: the master computer does not continuously send the desired pose signal to the master embedded computer and any of the slave embedded computers via the LAN router, and the respective slave embedded computers do not continuously send the actual pose signal to the master computer, and any of the slave computers does not send the motor position control signal to the surgical tool driving module/imaging tool driving module via the first communication bus at the same time.

Hereinafter, a method for detecting faults in the full operating state of a surgical robot and the incomplete operating state of the surgical robot of the present invention will be described in detail by two specific embodiments.

Embodiment 1

This embodiment describes a method for detecting faults in the full operating state of a surgical robot in detail, comprising:

1. the master computer broadcasts a desired pose signal to a master embedded computer and a plurality of slave embedded computers, respectively, via the LAN router at a preset period, and receives a null operation instruction signal transmitted from the master embedded computer at the preset period, and simultaneously receives actual pose signals transmitted from the respective slave embedded computers at the preset period;

2. the master embedded computer receives the desired pose signal transmitted from the master computer at the preset period, sends the null operation instruction signal to the master computer at the preset period and obtains a null operation response signal returned from the master computer; and simultaneously listens to motor position control signals transmitted from the respective slave embedded computers via the first communication bus;

3. the respective slave embedded computers receive the desired pose signal transmitted from the master computer via the LAN router at the preset period and transmit the actual pose signals to the master computer via the LAN router; and simultaneously send the motor position control signals to the surgical tool driving module/imaging tool driving module via the first communication bus at the preset period;

4. if neither of the master embedded computer and the slave embedded computers receives the desired pose signal transmitted from the master computer via the LAN router within the preset period and the master embedded computer does not receive the null operation response signal returned from the master computer via the LAN router, it is considered that the master computer fails in the full operating state;

5. if the master computer does not receive the null operating instruction signal transmitted from the master embedded computer via the LAN router within the preset period, it is considered that the master embedded computer fails in the full operating state;

6. if the master computer does not receive the actual pose signal transmitted from a certain slave embedded computer via the LAN router within the preset period and if the master embedded computer does not listen to the motor position control signal transmitted from said slave embedded computer via the first communication bus within the preset period, it is considered that said slave embedded computer fails in the full operating state.

Further, when the master computer fails, an alarm mechanism and an emergency stop mechanism are employed for the surgical robotic system, and after employing a recovery mechanism on the master computer, the master computer continues to send the signals via the LAN router to the master embedded computer and the respective slave embedded computers, and if the recovery mechanism of the master computer is unsuccessful, the master embedded computer executes a manual procedure and controls the slave embedded computers via the LAN router so as to control actions of the surgical tool/imaging tool.

Further, when the master embedded computer fails, after employing the alarm mechanism and the emergency stop mechanism for the surgical robotic system, the master computer executes the manual procedure, and thus controls actions of the surgical tool/imaging tool through the slave embedded computer.

Further, when the certain slave embedded computer fails, after employing the alarm mechanism and the emergency stop mechanism for the surgical robotic system, the master computer executes the manual procedure, the failed slave embedded computer is replaced with the main embedded computer, and the master computer controls actions of the surgical tool/imaging tool through the master embedded computer and the other slave embedded computers.

Further, the recovery mechanism of the present invention means that the master embedded computer waits for the master computer to restart and restore when the master computer fails, and after the master computer restores, the operator performs a status inquiry operation on the operation interface of the master computer, the master computer sends a status inquiry instruction to the master embedded computer via the LAN router, and adjusts the state of the surgical robotic system to a state prior to the failure after receiving the state response instruction transmitted from the main embedded computer.

Further, the alarm mechanism of the present invention is intended to attract attention of the operator, and in detail comprises:

1) when the master computer fails, the master embedded computer updates a corresponding master computer indicator light to an "error" display state via the second communication bus, and the second communication bus is preferably a two-wire serial bus, that is, an I2C bus;

2) when the master embedded computer fails, the master computer automatically switches the operation interface to the manual operation interface, prompts failure of the master embedded computer on the interface, and the master computer updates a corresponding master embedded computer indicator light to the "error" display state at the same time;

3) when the certain slave embedded computer fails, the master computer automatically switches the operation interface to the manual operation interface, and prompts failure of the certain slave embedded computer on the interface, and at this time the master embedded computer updates a corresponding slave embedded computer indicator light to "error" display state via the second communication bus.

Further, the emergency stop mechanism of the present invention refers to: the slave embedded computer controls the surgical tool and the imaging tool, through the corresponding surgical tool driving module/imaging tool driving module, to stop movement and maintain the current pose after receiving the "holding" command from the upper level computer, wherein the upper level computer can be the master computer or the main embedded computer.

Further, the manual procedure of the present invention refers to: directly controlling the master computer, the master embedded computer or the slave embedded computers through the joint-parameter manual adjustment region of the surgical robot, and in turn controlling actions of the surgical tool/imaging tool through the surgical tool driving module/imaging tool driving module. The process in detail is:

1) when the master computer fails, the master embedded computer switches to the manual operation interface, directly controls the respective slave embedded computers through the joint-parameter manual adjustment region, and thus controls actions of surgical tool/imaging tool through the surgical tool driving module/imaging tool driving module;

2) when the master embedded computer fails, the master computer switches to the manual operation interface, and directly controls the respective slave embedded computers through the joint-parameter manual adjustment region, and in turn controls actions of the surgical tool/imaging tool with the surgical tool driving module/imaging tool driving module;

3) when the certain slave embedded computer fails, the master computer switches to the manual operation interface, the master embedded computer takes over the failed slave embedded computer, and the master computer directly controls the master embedded computer and the remaining functional slave embedded computer through the joint-parameter manual adjustment region, and in turn controls actions of the surgical tool/imaging tool through the surgical tool driving module/imaging tool driving module.

Further, the upper level computer controls the surgical tool driving module and in turn controls actions of the surgical tool through the master embedded computer (used to take over the failed slave embedded computer) or the functional slave embedded computer.

For example, when the master computer fails, the master embedded computer is used as a master computer at this time, the operator operates the pose of the surgical tool driving module to be controlled in a mapping selection area of the joint-parameter manual adjustment region, the master embedded computer reads out the joint parameters of the surgical arm at the preset period and sends the generated desired pose to the slave embedded computers, the slave embedded computers receive the desired pose signal and perform closed-loop control of the pose of the surgical end effector at the end of the surgical tool through the surgical tool driving module, and thereby implement the operation of the surgical robot to safely withdraw a part of the surgical robot located in the patient's body to its initial position. The process in detail is as follows:

1) if the surgical arm carrying the surgical end effector at the end of the surgical tool is in an unfolded state, the surgical tool driving module drives the surgical end effector at the end of the surgical tool to maintain the current position and pose, and restore its initial state (e.g. when the surgical end effector is a surgical forceps, it should be restored its "closed" state), and thus drives the surgical arm back straight, then the process proceeds to step 2);

2) if the surgical end effector carried at the end of the surgical tool is not in its initial position and the surgical arm is in a straight state, the surgical tool driving module drives the surgical end effector at the end of the surgical tool to directly withdraw from the surgical incision on the patient to its initial position, and then the process proceeds to step 3);

3) the operator offloads the surgical tool from the surgical tool driving module to achieve separation of the surgical tool from the surgical robot.

Further, when the surgical tool is withdrawn from the surgical incision on the patient so as to achieve entire separation of the surgical tool from the surgical robot, the upper level computer controls the imaging tool driving module and in turn controls actions of the imaging tool through the master embedded computer (used to take over the failed slave embedded computer) or the functional slave embedded computers.

For example, when the certain slave embedded computer controlling actions of the imaging tool fails, the master embedded computer is used to take over the failed slave embedded computer, and the operator operates the surgical tool driving module to be controlled in the mapping selection area of the joint-parameter manual adjustment region, the master computer reads out the joint parameters of the surgical arm at the preset period and sends the generated desired pose to the main embedded computer, the main embedded computers receives the desired pose signal and performs closed-loop control of the pose of the imaging illumination module at the end of the imaging tool through the imaging tool driving module, and thereby implements operation of the surgical robot to safely withdraw a part of the imaging robot located in the patient's body to its initial position. The process in detail is as follows:

1) if the surgical arm carrying the imaging illumination module at the end of the imaging tool is in an unfolded state, the imaging tool driving module drives the imaging illumination module at the end of the imaging tool to maintain the current position and pose, thereby driving the surgical arm to straight back, and then the process proceeds to step 2);

2) if the imaging illumination module carried at the end of the imaging tool is not in its initial position and the surgical arm is in a straight state, the imaging tool driving module drives the imaging illumination module at the end of the imaging tool to directly withdraw from the surgical incision on the patient to its initial position, then the process proceeds to step 3);

3) the operator offloads the imaging tool from the imaging tool driving module to achieve separation of the imaging tool from the surgical robot.

Embodiment 2

This embodiment in detail describes a method for detecting faults in an incomplete operating state of a surgical robot, comprising:

1. A master computer sends a null operation instruction signal to a master embedded computer and a plurality of slave embedded computers, respectively, via the LAN router at a preset period, and receives null operation response signals transmitted from the master embedded computer and the slave embedded computers at the preset period.

2. The master embedded computer receives the null operation instruction signal transmitted from the master computer at the preset period and returns the null operation response signal to the master computer, and sends the null operation instruction signal to the slave embedded computers via the LAN router at the preset period and receives the null operation response signals returned from the respective slave embedded computers.

3. The respective slave embedded computers receive the null operation instruction signals transmitted from the master computer and the master embedded computer via the LAN router at the preset period and return the null operation response signals to the master computer and the master embedded computer at the preset period.

4. If neither of the master embedded computer and the slave embedded computers receives the null operation instruction signal transmitted from the master computer via the LAN router within the preset period, it is considered that the master computer fails in the incomplete operating state.

5. If the master computer does not receive the null operating response signal returned from the master embedded computer via the LAN router within the preset period and the respective slave embedded computers does not receive the null operating instruction signal transmitted from the master embedded computer within the preset period, it is considered that the master embedded computer fails in the incomplete operating state.

6. If the master computer does not receive the null operating response signal returned from a certain slave embedded computer via the LAN router within the preset period and if the master embedded computer does not receive the null operating response signal returned from said slave embedded computer within the preset period, it is considered that said slave embedded computer fails in the incomplete operating state.

Further, when the master computer, the master embedded computer or the certain embedded computer fails in the incomplete operating state, the alarm mechanism, the recovery mechanism, the manual procedure and the operation processes thereof are almost same as those in Embodiment 1, except that the master computer, the master embedded computer or the certain slave embedded computer only utilizes the alarm mechanism when they fail in the incomplete operating state, and no emergency stop mechanism is adopted. In addition, the operational principles of the alarm mechanism, the recovery mechanism, and the manual procedure in this embodiment are completely same as those in Embodiment 1, and details are not described again herein.

Further, the upper level computer controls the surgical tool driving module and in turn controls actions of the surgical tool through the master embedded computer (used to take over the failed slave embedded computer) or the functional slave embedded computers, and this process is almost same as that in Embodiment 1. Because the surgical robot is in the incomplete operating state, some differences exist in the process of safely withdrawing the surgical tool of the surgical robot to its initial position as following:

1) if the surgical arm carrying the surgical end effector at the end of the surgical tool is in an unfolded state, the surgical tool driving module drives the surgical arm to straight back, and then the process proceeds to step 2);

2) if the surgical end effector carried at the end of the surgical tool is not in its initial position and the surgical arm is in a straight state, the surgical tool driving module drives the surgical end effector at the end of the surgical tool to be directly withdrawn from the surgical incision on the patient to its initial position, and then the process proceeds to step 3);

3) the operator offloads the surgical tool from the surgical tool driving module to achieve separation of the surgical tool from the surgical robot.

Further, when the surgical tool is withdrawn from the surgical incision on the patient and entire separation of the surgical tool from the surgical robot is achieved, the upper level computer controls the imaging tool driving module and in turn controls actions of the imaging tool through the master embedded computer (used to take over the failed slave embedded computer) or the functional slave embedded computer, and this process is almost same as that in Embodiment 1. Because the surgical robot is in the incomplete operating state, some differences exist in the process of safely withdrawing the imaging tool of the surgical robot to its initial position as following:

1) if the surgical arm carrying the imaging illumination module at the end of the surgical tool is in an unfolded state, the imaging tool driving module drives the surgical arm to straight back, and then the process proceeds to step 2);

2) if the imaging illumination module carried at the end of the surgical tool is not in its initial position and the surgical arm is in a straight state, the imaging tool driving module drives the imaging illumination module at the end of the surgical tool to be directly withdrawn from the surgical incision on the patient to its initial position, and then the process proceeds to step 3);

3) the operator offloads the imaging tool from the imaging tool driving module to achieve separation of the imaging tool from the surgical robot.

The above embodiments are only used to illustrate the present invention, and various implementing steps of the methods may be changed. Any equivalent transformations and improvements based on the technical solution of the present invention should not be excluded from the protection scope of the present invention.

The invention claimed is:

1. A system, comprising:
   a master computer;
   a master embedded computer; and
   a plurality of slave embedded computers, wherein each of the plurality of slave embedded computers is configured to:
      transmit an actual pose signal to the master computer;
      transmit a motor position control signal to a surgical tool hardware driver or an imaging tool hardware driver;
   wherein the master embedded computer is configured to:
      listen to motor position control signals transmitted from the plurality of slave embedded computers; and
      replace one of the plurality of slave embedded computers when the master computer does not receive the actual pose signal transmitted by that slave embedded computer and the master embedded computer does not find the motor position control signal transmitted from that slave embedded computer.

2. The system according to claim 1, wherein:
   the master computer is configured to:
      send a master computer signal to the master embedded computer and the plurality of slave embedded computers; and
      execute a restore procedure when the master embedded computer and the plurality of slave embedded computers do not receive the master computer signal; and
   the master embedded computer is configured to execute an alarm mechanism when the master embedded computer and the plurality of slave embedded computers do not receive the master computer signal.

3. The system according to claim 2, wherein:
   the master computer signal comprises a target pose signal for controlling a pose of a surgical end effector at an end of a surgical tool through the surgical tool hardware driver or a pose of an imaging illumination hardware tool at an end of an imaging tool through the imaging tool hardware driver;
   the master embedded computer is configured to send a null operation instruction signal to the master computer;
   the master computer is further configured to:
      return a null operation response signal to the master embedded computer; and
      execute the restore procedure when the master embedded computer does not receive the null operation response signal; and
   the master embedded computer is further configured to execute the alarm mechanism when the master embedded computer does not receive the null operation response signal.

4. The system according to claim 3, wherein the master computer is configured to execute a manual procedure when the master computer does not receive the null operation instruction signal.

5. The system according to claim 2, wherein:
   the master computer signal comprises a first null operation instruction signal;
   the master embedded computer is configured to:
      return a first null operation response signal to the master computer; and
      send a second null operation instruction signal to the plurality of slave embedded computers; and
   the master computer is configured to execute a manual procedure when the master computer does not receive the first null operating response signal and the plurality of slave embedded computers do not receive the second null operating instruction signal.

6. The system according to claim 5, wherein:
   at least one of the plurality of slave embedded computers is configured to:
      return a second null operation response signal to the master computer; and
      return a third null operation response signal to the master embedded computer; and
   the master embedded computer is configured to replace the at least one of the plurality of slave embedded computers when the master computer does not receive the second null operation response signal returned from the at least one of plurality of slave embedded computers and the master embedded computer does not receive the third null operation response signal returned from the at least one of the plurality of slave embedded computers.

7. The system according to claim 2, comprising a surgical robot system configured to perform one or more of an alarm procedure, an emergency stop procedure, or a recovery procedure when the master computer, the master embedded computer, or at least one of the plurality of slave embedded computers.

8. The system according to claim 7, wherein:
   the surgical robot system is configured to perform the recovery procedure on the master computer when the master computer has a failure, and the master embedded computer is configured to execute a first manual procedure to control the plurality of slave embedded computers to control a surgical tool or an imaging tool when the recovery procedure is unsuccessful; or
   the master computer is configured to perform a second manual procedure to control the surgical tool or the imaging tool through the plurality of slave embedded computers when the master embedded computer has a failure; or
   the master computer is further configured to perform a third manual procedure to replace the failed at least one slave embedded computer with the master embedded computer and control the surgical tool or the imaging tool through the master embedded computer or another slave embedded computer when at least one of the plurality of slave embedded computers has a failure.

9. The system according to claim 7, wherein the recovery procedure comprises: when the master computer has a failure, the master embedded computer waits for the master computer to restore, and the master computer sends, after the restore, a status inquiry instruction to the master embedded computer and adjusts a state of the surgical robot system to a previous state prior to the failure after receiving a state response instruction transmitted from the master embedded computer.

10. The system according to claim 7, wherein the alarm procedure comprises at least one of:
   when the master computer has a failure, the master embedded computer updates a corresponding master computer indicator light to an "error" display state via a communication bus;
   when the master embedded computer has a failure, the master computer switches an operation interface to a first manual operation interface, prompts the failure of the master embedded computer on the first manual operation interface, and updates a corresponding master embedded computer indicator light to an "error" display state; or when at least one of the plurality of slave embedded computers has a failure, the master computer switches the operation interface to a second manual operation interface, prompts the failure of the at least one of the plurality of slave embedded computers on the second manual operation interface, and the master embedded computer updates at least one corresponding slave embedded computer indicator light to an "error" display state via the communication bus.

11. The system according to claim 7, wherein the emergency stop procedure comprises:

the at least one of the plurality of slave embedded computers controls a surgical tool or an imaging tool, with the corresponding surgical tool hardware driver or an imaging tool hardware driver, to stop movement and maintain a current pose; or the master embedded computer, instead of the failed at least one slave embedded computer, controls the surgical tool or the imaging tool, with the corresponding surgical tool hardware driver or imaging tool hardware driver, to stop movement and maintain the current pose.

12. The system according to claim 8, wherein:

the first manual procedure includes that the master embedded computer switches to a third manual operation interface and controls the plurality of slave embedded computers to control the surgical tool or the imaging tool with a surgical tool hardware driver or an imaging tool hardware driver; or the second manual procedure includes that the master computer switches to a fourth manual operation interface, and controls the plurality of slave embedded computers to control the surgical tool or the imaging tool with the surgical tool hardware driver or the imaging tool hardware driver; or the third manual procedure includes that the master embedded computer takes over the failed slave embedded computer, and the master computer switches to a fifth manual operation interface, and controls the master embedded computer and remaining functional slave embedded computers to control the surgical tool or the imaging tool with the surgical tool hardware driver or the imaging tool hardware driver.

13. The system according to claim 2, wherein the master computer or the master embedded computers is configured to:

when a surgical arm carrying a surgical end effector at an end of a surgical tool is in an unfolded state, drive, with the surgical tool hardware driver, the surgical end effector to maintain a current position and pose, restore an initial state, and drive the surgical arm back straight; and when the surgical end effector is not in an initial position and the surgical arm is in a straight state, drive, with the surgical tool hardware driver, the surgical end effector to be withdrawn from a surgical incision in a patient back to the initial position;

or when a surgical arm carrying an imaging illumination hardware tool at an end of an imaging tool is in an unfolded state, drive, with the imaging tool hardware driver, the imaging illumination hardware tool to maintain a current position and pose, and drive the surgical arm to straight back; and when the imaging illumination hardware tool is not in an initial position and the surgical arm is in a straight state, drive, with the imaging tool hardware driver, the imaging illumination hardware tool to be withdrawn from a surgical incision in a patient to the initial position.

14. A method for detecting faults in a system comprising a master computer, a master embedded computer and a plurality of slave embedded computers, the method comprising:

transmitting, by each of the plurality of slave embedded computers, an actual pose signal to the master computer;

sending, by each of the plurality of slave embedded computers, a motor position control signal to a surgical tool hardware driver or an imaging tool hardware driver;

listening, by the master embedded computer, to motor position control signals transmitted from the plurality of slave embedded computers; and replacing one of the plurality of slave embedded computers by the master embedded computer when the master computer does not receive the actual pose signal transmitted by that slave embedded computer and the master embedded computer does not find the motor position control signal transmitted from that slave embedded computer.

15. The method according to claim 14, further comprising:

sending, by the master computer, a master computer signal to the master embedded computer and the plurality of slave embedded computers; and executing a restore procedure by the master computer or an alarm mechanism by the master embedded computer, when the master embedded computer and the plurality of slave embedded computers do not receive the master computer signal.

16. The method according to claim 15, wherein the master computer signal comprises a target pose signal for controlling a pose of a surgical end effector at an end of a surgical tool through the surgical tool hardware driver or a pose of an imaging illumination hardware tool at an end of an imaging tool through the imaging tool hardware driver, and the method further comprises:

sending, by the master embedded computer, a null operation instruction signal to the master computer;

returning, by the master computer, a null operation response signal to the master embedded computer; and executing the restore procedure by the master computer or an alarm mechanism by the master embedded computer, when the master embedded computer does not receive the null operation response signal.

17. The method according to claim 16, further comprising:

executing a manual procedure by the master computer, when the master computer does not receive the null operation instruction signal.

18. The method according to claim 15, wherein the master computer signal comprises a first null operation instruction signal, and the method further comprises:

returning, by the master embedded computer, a first null operation response signal to the master computer;

sending, by the master embedded computer, a second null operation instruction signal to the plurality of slave embedded computers; and executing a manual procedure by the master computer, when the master computer does not receive the first null operating response signal and the plurality of slave embedded computers do not receive the second null operating instruction signal.

19. The method according to claim 18, further comprising:
- returning, by at least one of the plurality of slave embedded computers, a second null operation response signal to the master computer;
- returning, by the at least one of the plurality of slave embedded computers, a third null operation response signal to the master embedded computer; and
- replacing the at least one of the plurality of slave embedded computers by the master embedded computer, when the master computer does not receive the second null operation response signal returned from the at least one of the plurality of slave embedded computers and the master embedded computer does not receive the third null operation response signal returned from the at least one of the plurality of slave embedded computers.

20. The method according to claim 15, further comprising:
- performing, by a surgical robot system, at least one of an alarm procedure, an emergency stop procedure, or a recovery procedure when the master computer, the master embedded computer, or at least one of the plurality of slave embedded computers has a failure.

* * * * *